United States Patent [19]
Raatikainen

[11] Patent Number: 5,721,759
[45] Date of Patent: Feb. 24, 1998

[54] METHOD AND EQUIPMENT FOR DETERMINING THE CONTENT OF AN ELEMENT

[75] Inventor: Jukka Raatikainen, Espoo, Finland

[73] Assignee: IMA Engineering Ltd. Oy, Espoo, Finland

[21] Appl. No.: 817,883

[22] PCT Filed: Nov. 13, 1995

[86] PCT No.: PCT/FI95/00621

§ 371 Date: May 1, 1997

§ 102(e) Date: May 1, 1997

[87] PCT Pub. No.: WO96/15442

PCT Pub. Date: May 23, 1996

[30] Foreign Application Priority Data

Nov. 14, 1994 [FI] Finland ..................... 945364

[51] Int. Cl.⁶ ................................. G01T 1/36
[52] U.S. Cl. ........................... 378/47; 378/44
[58] Field of Search ..................... 378/44, 45, 47, 378/48, 49, 50, 51, 53, 56

[56] References Cited

U.S. PATENT DOCUMENTS

| | | |
|---|---|---|
| 4,015,124 | 3/1977 | Page .......................... 378/45 |
| 4,045,676 | 8/1977 | Rolle .......................... 378/48 |

FOREIGN PATENT DOCUMENTS

| | | |
|---|---|---|
| 51872 | 12/1976 | Finland . |
| 0204357 | 11/1983 | Japan ..................... 378/44 |
| 60-61649 | 4/1985 | Japan . |

*Primary Examiner*—Don Wong
*Attorney, Agent, or Firm*—Young & Thompson

[57] ABSTRACT

The invention relates to a method and an equipment for determining the content of an element from a flowing sample mass (1) by utilizing x-ray fluorescence, in which method the sample mass (1) is irradiated with x-ray or gamma radiation; the radiation emitted by the sample mass is detected; an energy-dispersive radiation spectrum of the radiation emitted by the sample mass is determined; and the content of the element is determined from the measured radiation spectrum on the basis of the intensity of the radiation spectrum window characteristic of this element. In order that the method and equipment would also be applicable in field conditions, the method farther comprises steps in which air temperature is measured in the air space between the sample mass (1) and a radiation detector or detectors (5); the first correction coefficient dependent on the measured air temperature is determined; and the determined content of the element is corrected by said first correction coefficient in order to compensate the attenuation of the characteristic radiation in the air between the sample mass (1) and the radiation detector or detectors (5).

10 Claims, 2 Drawing Sheets

METHOD AND EQUIPMENT FOR DETERMINING THE CONTENT OF AN ELEMENT

FIELD OF THE INVENTION

The present invention relates to a method for determining the content of an element from a flowing sample mass by utilizing x-ray fluorescence, in which method the sample mass is irradiated with x-ray or gamma radiation, the radiation emitted by the sample mass is detected, an energy-dispersive radiation spectrum of the radiation emitted by the sample mass is determined, and the content of the element is determined from the measured radiation spectrum on the basis of the intensity of the radiation spectrum window characteristic of this element.

BACK OF THE INVENTION

A detector in a measuring equipment utilizing x-ray fluorescence detects photons which develop into an energy-dispersive radiation spectrum (intensity) as a function of wave length or energy from which sequences representing each element are selected by means of electronics and/or software. These sequences are known as energy windows, i.e. channels. The pulses (intensities) gathered to the channels are used in analytical calculation. Several so called background channels or scattering channels in different energy areas are also selected from the spectrum by means of which channels information is gathered on the total amount of the mass to be measured and its distance with respect to the detectors.

Analytical methods based on x-ray fluorescence can be applied in an industrial process for determining the element content of a flowing sample mass. By means of the method, the elements can be measured directly from the mass flow, the amount of which can vary. In a typical solution, elements of crushed ore are measured directly from above a conveyor. Various mineral concentration plants, quarries, cement industry and other branches of chemical industry need exactly this kind of a method for measuring elements directly from the process flow. Generally, the object is to perform the measurement at such accuracy and speed that the process can be controlled and adjusted in real time by means of the obtained measuring result.

Element analyzers based on x-ray fluorescence are widely used in laboratories. The measurement of a fine-crushed sample is increasingly performed by means of process analyzers which cannot, however, be used for measuring a material which typically has a larger granular size than 1 mm.

Nowadays there are also in use apparatuses and methods based on x-ray fluorescence for measuring elements directly from above a belt or through a belt from a mass flow. For example, Ima Engineering Ltd. Oy, Espoo, Finland manufactures and sells Beltcon 100 and Beltcon 200 analyzers for the above-mentioned purposes. A problem of both apparatuses is especially the inaccuracy of their measurement results in varying environmental conditions. Especially the measuring of light elements, such as calcium by means of a fixedly installed measuring equipment has been found to be difficult as the intensity of the characteristic x-ray radiation attenuates in proportion to the square of distance. Therefore, the measuring distance should be as small as possible when measuring light elements, such as Ca, K, Si and Al.

The object of the present invention is to measure and analyze accurately the element contents of crushed and/or fine-crushed ore by means of the x-ray fluorescence principle in real time directly from above the conveyor so that it is possible to adjust the process in real time on the basis of the element contents.

SUMMARY OF THE INVENTION

The object of the present invention is also to compensate automatically the variations in the distance between the mass and the measuring equipment, as well as the changes in the conditions of the measuring environment.

Another object of the invention is to ensure the ability of the measuring equipment to function against both momentary and long-term variations.

A further object of the invention is to measure even light elements reliably and accurately.

Still another object of the invention is to disclose a method and equipment with which element contents can be measured and analyzed by means of the x-ray fluorescence principle from a mass flow which can be solid, slurry or liquid matter.

In order to solve the above-mentioned problems and to achieve the objects, the method of the invention further comprises steps in which air temperature is measured in the air space between the sample mass and a radiation detector or detectors, a first correction coefficient dependent on the measured air temperature is determined, and the determined content of the element is corrected by said first correction coefficient in order to compensate the attenuation of the characteristic radiation in the air between the sample mass and the radiation detector or detectors.

It has been further detected that air humidity, air pressure, dust content and changes in the content of a certain gas component have an effect on the accuracy of the measuring result. According to the invention, these variables can also be measured, when desired, and the relevant correction coefficients can be determined, by means of which coefficients the measuring result is further corrected in addition to the temperature correction.

In order that the changes in the distance between the sample mass and the detector or detectors could be compensated more accurately than before and on the other hand, that as small a distance as possible could be maintained between the sample mass and the detectors, the method of the invention further comprises a step in which the distance between the sample mass and the radiation detector or detectors is essentially standardized by levelling the surface of the flowing sample mass and/or by measuring said distance and adjusting the distance of the radiation detector or detectors from the sample mass on the basis of said measuring result.

By means of the method and equipment of the invention, temperature changes and other variations in environmental conditions can be taken into consideration in the measuring state. This has proved to be very significant since the intensities of lighter elements are exponentially attenuated as a function of temperature and dust content.

Although the method and equipment of the invention are especially suitable for a fast measuring of elements of crushed and fine-crushed ore directly on top of a conveyor, the method and equipment can be used also in diverse arrangements of mass industry in which sampling is difficult, slow and expensive, the samples are non-homogeneous in their element contents and the amount of mass on the conveyor varies.

BRIEF DESCRIPTION OF THE DRAWINGS

In the following, the method and equipment of the invention are described in more detail with reference to the accompanying drawings, in which.

DETAILED DESCRIPTION OF THE PREFERRED EMBODIMENT

Figure 1:
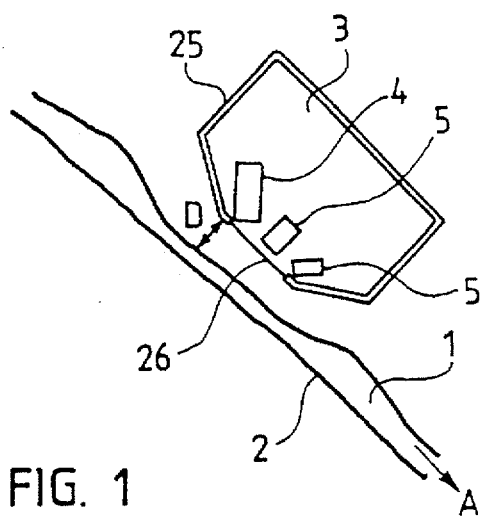
FIG. 1 illustrates in a schematic diagram how the measuring equipment is disposed in relation to the mass flow to be measured.
Figure 2:
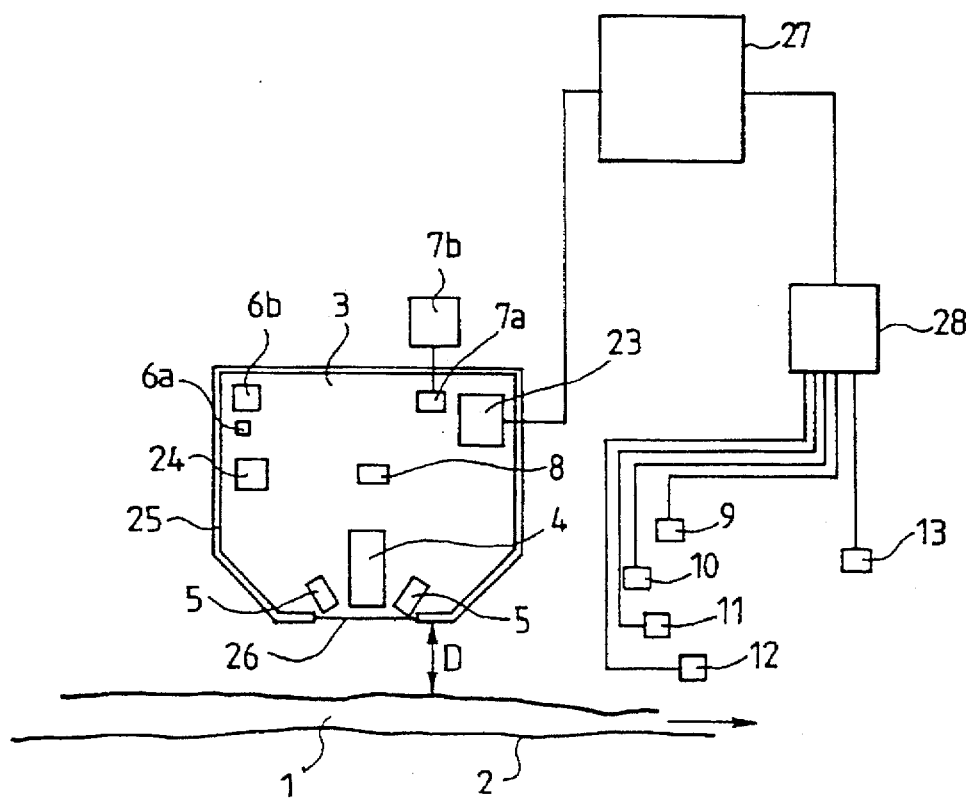
FIG. 2 illustrates a schematic diagram of the measuring equipment and the sensors used for compensation.

The measuring equipment shown in FIG. 1, which is generally marked with reference numeral 3, is installed in the immediate proximity of a mass 1 on a base 2. The mass can be crushed and/or fine-crushed mineral and the base 2 can be a belt conveyor, for instance. Typically, either the mass or the base is in motion which means that it is a question of a mass flow. It is also possible for the method and equipment of the invention that the flow of the mass is interrupted for the duration of measuring, but halting is often not possible simply because of the great amounts of mass on the conveyor and nor is it necessary for the operation of the method and equipment of the invention.

The direction of motion in FIG. 1 is marked with a direction arrow A. The mass 1 can be solid, slurry or liquid matter. The element content of the mass can vary greatly. The amount of the mass flow to be measured can also vary greatly and it can contain particles, such as boulders, the size of which varies from one boulder to another. The element content of the boulders can also vary between boulders. When the amount of the mass on the base can vary, a distance D from the surface of the mass to the measuring equipment can also vary.

The measuring equipment 3 comprises one or more x-ray or gamma radiation sources 4 and one or more radiation detectors 5 which are disposed at a preferred distance D from the mass flow to be measured. The radiation source can be for example an x-ray tube or a radioactive isotope radiator. The radiation detector 5 can be a scintillator, a proportional counter or a semiconductor detector. If there are more detectors, one of them can be more sensitive to the characteristic x-ray radiation of light elements and some other to the x-ray radiation of heavy elements. More radiation sources and/or detectors are used when all the elements to be measured cannot be excited and detected efficiently enough with one radiation source and/or detector, or when measuring coarse mass granules, whereby a more reliable measuring result is obtained by measuring and irradiating from several directions.

The measuring equipment 3 also comprises electronics 23 required for the detection of radiation; a computer and software 27 for computing the results; a measuring sensor 6a for internal temperature and an air conditioner 6b for standardizing the internal temperature; when needed, a feeding device 7a for extrusion gas and an auxiliary tank for rinsing the gas component which disturbs the measuring; a humidity sensor 8 for measuring air humidity inside the measuring equipment; safety, measuring and control electronics 24; a mechanical body and a tight casing 25; easily radiation-penetrating windows 26 in front of the radiation sources 4 and detectors 5 attached either to the body, the casing or the component in question. The internal sensors and regulating units of the measuring equipment 3 are connected electrically to the safety, measuring and control electronics 24 which is again connected electrically and by means of software to the computer 27. The electronics 23 used for detecting radiation is connected electrically and by means of software to the computer 27.

According to the invention, the measuring equipment also comprises means for measuring the external conditions in the air space between the sample mass 1 and the detectors 5. These meters are a measuring sensor 9 for external temperature, a measuring sensor 10 for external air pressure, a measuring sensor 11 for external humidity, a measuring sensor 12 for external dust content and a measuring sensor 13 for external disturbing gas component. The above-mentioned measuring sensors are disposed in the immediate proximity of the measuring point so that they present the conditions in the measuring point correctly, whereby the measuring data they provide can be used for correcting the characteristic x-ray radiation intensities measured from the samples by using calculation formulae. The external measuring sensors 9 to 13 are connected via one or more signal processing units 28 to the computer 27.

The measuring variables, which describe the external conditions measured according to the invention and which report on the environmental conditions in the space between the sample to be measured and the measuring equipment 3, are used for calculating various correction coefficients by means of which it is possible to compensate the effect of these external variables on the determined x-ray radiation intensities for different elements. The starting point is then that the air between the sample 1 to be measured and the detecting means 5 attenuates the radiation emitted by the sample depending on the conditions in which the air is. In practice, it has been noted that these environmental factors and especially air temperature have a significant effect on the measuring result when measuring light elements. The intensities obtained as a measuring result in conjunction with light elements may remain very low, whereby an attenuation with even a small absolute value may distort the measuring result significantly.

The most essential correction of the invention is the temperature correction. In connection with the temperature correction, an attenuation coefficient $\mu_1$ dependent on the temperature is first calculated with the formula:

$$\mu_1 = K_E/T,$$

in which $K_E$ is a material-specifically calculated constant and T is the temperature. The temperature corrected intensity $I_E$ can then be calculated with the formula:

$$I_E = N_E * e^{\mu_1 x}$$

in which $N_E$ is a unitized intensity and x is distance (cm).

If air density and also, the measuring distance are assumed to remain constant and only the temperature changes from the value of 20° C. to 30° C., the intensity changes 4.3%. This change of 10 degrees is very small when considering mining conditions but on the other hand, a change of 4.3% in the measuring result is very significant.

The equations described above can also be deduced for other variables which should possibly be taken into consideration in the compensation, and which variables have an effect on the attenuation of the x-ray radiation in the air between the sample mass and the radiation detector. In practice, the effect of these measured variables on the attenuation can be determined as correction coefficients which are calculated in order to correct the intensity measuring results obtained for use in the block 28. As has already been stated earlier, air temperature has the most significant effect on the measuring result. Humidity and air pressure have the second most important effect. Of course, an essential dust content may also have a very significant effect on the attenuation of the air space.

Naturally, the distance the detector has from the sample also has a significant effect on the amount of attenuation in the air space. Therefore, when measuring light elements, it is preferable to minimize said distance which is marked with the reference D in FIGS. 1 to 4. In order to render this distance as small as possible and also, as constant as possible, FIGS. 3 and 4 show two different embodiments of the invention by means of which the distance in question will be essentially standardized.

Figure 3:
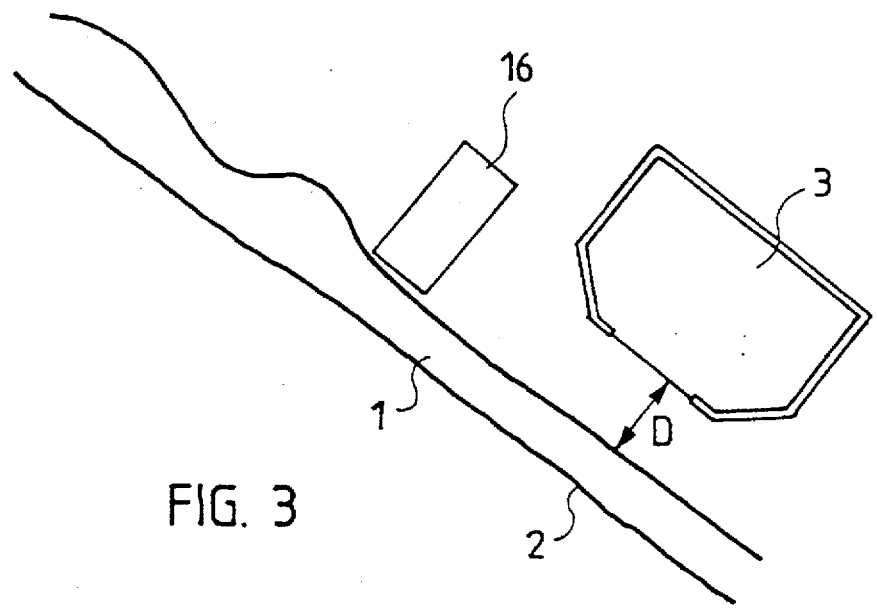
FIG. 3 illustrates a schematic diagram of a first embodiment of a distance standardizing arrangement.

FIG. 3 shows an arrangement in which the surface of the sample mass 1 is levelled with a leveller 16 so that the surface is at a constant distance from the measuring equipment 3. The leveller is used in this way when the sample mass is of relatively fine division. In case of rather coarse granules or even boulders, the leveller 16 cannot be applied as then the force concentrated on the belt 2 through the sample mass 1 would grow unreasonably great. Naturally, the use of the leveller 16 also requires a relatively even sample mass flow. If the sample mass varies greatly with time, the equalizing effect required would be so great that it is no longer obtainable in practice.

Figure 4:
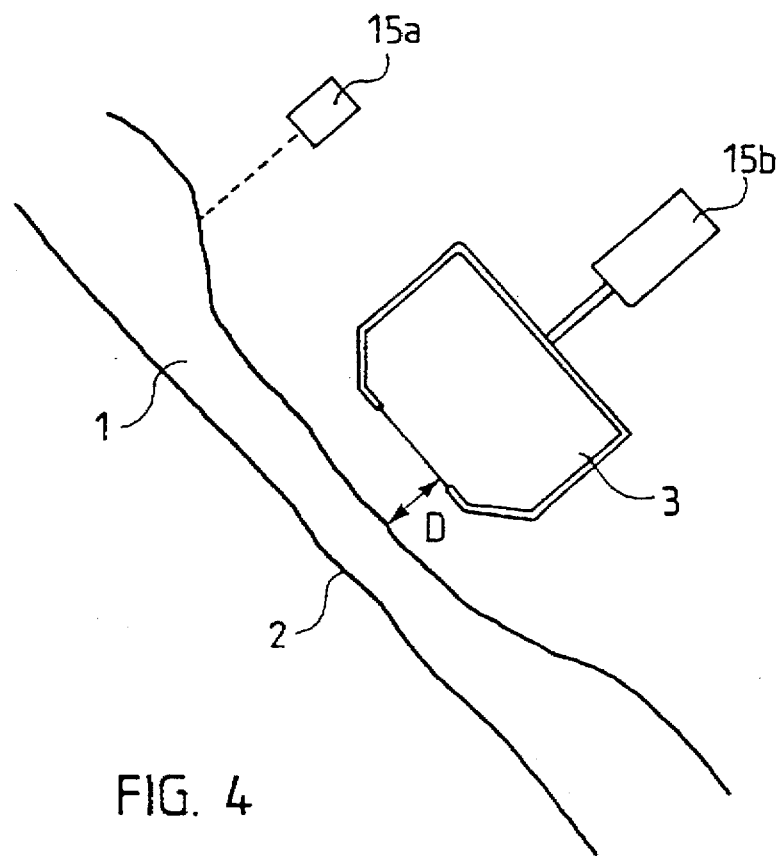
FIG. 4 illustrates a schematic diagram of a second embodiment of a distance standardizing arrangement.

FIG. 4 shows another arrangement for standardizing the measuring distance which is applied also when the sample mass consists of boulders or is coarse or when its amount varies significantly with time. In this arrangement of FIG. 4, the distance of the sample mass from the measuring sensor is measured with a sensor 15a at a distance before the measuring equipment 3. On the basis of this measuring result, the distance of the measuring equipment 3 from the conveyor belt 2 is then adjusted by using e.g. a hydraulic cylinder 15b, so that the distance of the measuring device 3 from the surface of the sample mass 1 remains as constant as possible. In this context, it should be remembered that normally the measurement of the whole energy-dispersive radiation spectrum is carried out by the measuring equipment 3 and the distance the measuring equipment has from the sample mass 1 can be determined from this spectrum on the basis of background radiation. The measuring results can also be corrected on the basis of this measurement. However, it is not possible to make this correction for light elements if the measuring distance is not small enough to obtain a reasonable measuring result despite various attenuating factors.

In order to achieve a reliable result when the mass is in motion, the measuring has to be arranged into short measuring sequences from which e.g. average results are calculated. Statistically more reliable results are obtained and a greater volume of the sample is measured when measuring is performed simultaneously from various directions, that is, by using more detectors by means of which radiation from different directions is measured from the sample mass.

As was stated earlier, in addition to the characteristic energy windows of the examined elements, so called background channels, that is, scattering channels are selected from the radiation spectrum. The analytical calculation is based on calculation formulae which include the measured intensity and the scattering intensities of the element in question. The calculation formula is obtained by means of calibration measurements by using in a regression analysis the measured intensities and contents of the elements and the scattering background of known samples. When measuring coarse samples, there can be several detectors positioned at different measuring angles so that representative measuring intensities are also obtained from a granular sample mass. Several radiation sources can be used for the same purpose. When measuring both light and heavy elements, more radiation sources or one adjustable radiation source can be used from which source several different excitation energies are thus derived. In the measuring method, short-term or long-term changes inside the equipment are compensated by standardizing the internal conditions of the actual measuring equipment, as was shown earlier, and by measuring an external and/or internal reference sample. Reference measuring compensates the drift of internal electronics and the effect of external humidity and dust. The intensity of reference measuring is compared to the original reference intensities measured at the time of calibration and the information obtained is used for calculating a correction coefficient for the measured intensities.

The method and equipment of the invention is above illustrated by means of some embodiments by way of example and it is to be understood that some changes may be made thereto without deviating from the scope defined by the appended claims.

I claim:

1. A method for determining the content of an element from a flowing sample mass (1) by utilizing x-ray fluorescence, in which method the sample mass (1) is irradiated with x-ray or gamma radiation, the radiation emitted by the sample mass is detected, an energy-dispersive radiation spectrum of the radiation emitted by the sample mass is determined, and the content of the element is determined from the measured radiation spectrum on the basis of the intensity of the radiation spectrum window characteristic of this element, air temperature is measured in the air space between the sample mass (1) and a radiation detector or detectors (5), a first correction coefficient dependent on the measured air temperature is determined, and the determined content of the element is corrected by said first correction coefficient in order to compensate the attenuation of the characteristic radiation in the air between the flowing sample mass (1) and the radiation detector or detectors (5), characterized in that said method further comprises steps in which the dust content is measured in the air space between the sample mass (1) and the radiation detector or detectors (5), a second correction coefficient dependent on the measured dust content is determined, and the determined content of the element is corrected by said second correction coefficient in order to compensate the attenuation of the characteristic radiation in the air between the flowing sample mass (1) and the radiation detector or detectors (5).

2. A method according to claim 1, characterized in that said method further comprises steps in which the background radiation is measured, a distance between the radiation detector or detectors (5) and the flowing sample mass is determined on the basis of the determined energy-dispersive radiation spectrum and the background radiation, a third correction coefficient dependent on the determined distance is determined, and the determined content of the element is corrected by said third correction coefficient in order to compensate the variation in distance between the flowing sample mass and the radiation detector or detectors (5).

3. A method according to claim 1, characterized in that said method further comprises steps in which air humidity is measured in the air space between the sample mass (1) and the radiation detector or detectors (5), a fourth correction coefficient dependent on the measured air humidity is determined, and the determined content of the element is corrected by said fourth correction coefficient in order to compensate the attenuation of the characteristic radiation in the air between the sample mass (1) and the radiation detector or detectors (5).

4. A method according to claim 1, characterized in that said method further comprises steps in which air pressure is measured in the air space between the sample mass (1) and the radiation detector or detectors (5), a fifth correction coefficient dependent on the measured air pressure is determined, and the determined content of the element is corrected by said fifth correction coefficient in order to compensate the attenuation of the characteristic radiation in the air between the sample mass (1) and the radiation detector or detectors (5).

5. A method according to claim 1, characterized in that said method further comprises steps in which the content of a certain gas component is measured in the air space between the sample mass (1) and the radiation detector or detectors (5), a sixth correction coefficient dependent on the measured gas component content is determined, and the determined content of the element is corrected by said sixth correction coefficient in order to compensate the attenuation of the characteristic radiation in the air between the sample mass (1) and the radiation detector or detectors (5).

6. Art equipment for determining the content of an element from a flowing sample mass by utilizing x-ray fluorescence, which equipment comprises at least one x-ray or gamma radiation source (4) for irradiating the sample mass (1), detection means (5) for detecting the radiation emitted by the sample mass, means (27) for determining the energy-dispersive radiation spectrum of the radiation emitted by the sample mass and for determining the content of the element from this radiation spectrum on the basis of the intensity of the radiation spectrum window characteristic of this element, means (9) for measuring air temperature in the air space between the sample mass (1) and the detection means (5), means (28) for determining a first correction coefficient dependent on the measured air temperature, and means (27) for correcting the determined content of the element by said first correction coefficient in order to compensate the attenuation of the characteristic radiation in the air between the sample mass (1) and the detection means (5), characterized in that said equipment further comprises means (12) for measuring the dust content in the air space between the sample mass (1) and the detection means (5), means (28) for determining a second correction coefficient dependent on the measured dust content, and means (27) for correcting the determined content of the element by said second correction coefficient in order to compensate the attenuation of the characteristic radiation in the air between the sample mass (1) and the detection means (5).

7. An equipment according to claim 6, characterized in that said equipment further comprises means for measuring the background radiation, means for determining the distance between the radiation detector or detectors (5) and the flowing sample mass is determined on the basis of the determined energy-dispersive radiation spectrum and the background radiation, a third correction coefficient dependent on the determined distance is determined, and the determined content of the element is corrected by said third correction coefficient in order to compensate the variation in distance between the flowing sample mass and the radiation detector or detectors (5).

8. An equipment according to claim 6, characterized in that said equipment further comprises means (11) for measuring air humidity in the air space between the sample mass (1) and the detection means (5), means (28) for determining a fourth correction coefficient dependent on the measured air humidity, and means (27) for correcting the determined content of the element by said fourth correction coefficient in order to compensate the attenuation of the characteristic radiation in the air between the sample mass (1) and the detection means (5).

9. An equipment according to claim 6, characterized in that said equipment further comprises means (10) for measuring air pressure in the air space between the sample mass (1) and the detection means (5), means (28) for determining a fifth correction coefficient dependent on the measured air pressure, and means (27) for correcting the determined content of the element by said fifth correction coefficient in order to compensate the attenuation of the characteristic radiation in the air between the sample mass (1) and the detection means (5).

10. An equipment according to claim 6, characterized in that said equipment further comprises means (13) for measuring the content of a certain gas component in the air space between the sample mass (1) and the detection means (5), means (28) for determining a sixth correction coefficient dependent on the measured gas component content, and means (27) for correcting the determined content of the element by said sixth correction coefficient in order to compensate the attenuation of the characteristic radiation in the air between the sample mass (1) and the detection means (5).

* * * * *